United States Patent [19]

Rao et al.

[11] Patent Number: 4,605,667

[45] Date of Patent: Aug. 12, 1986

[54] PESTICIDAL WATER-SOLUBLE AMINOACID SULFENYLATED CARBAMATES

[75] Inventors: Chennupati K. Rao, Bhopal, India; Themistocles D. D'Silva, Chapel Hill, N.C.

[73] Assignee: Union Carbide Corporation, Danbury, Conn.

[21] Appl. No.: 717,544

[22] Filed: Mar. 29, 1985

[51] Int. Cl.[4] .................. A01N 47/10; A01N 37/34; C07C 119/18; C07C 149/43

[52] U.S. Cl. ............................. 514/477; 558/391; 560/16; 560/29; 560/32; 560/142; 560/145; 560/134; 564/40; 514/480; 514/481; 514/478; 514/487; 514/482; 514/490; 549/30; 549/365; 549/441; 549/452; 549/448; 548/454

[58] Field of Search ........ 260/453 RW, 453.3, 465 D, 260/465.4; 560/16, 29, 32, 142, 145, 134; 564/40; 514/477, 480, 481, 478, 487, 482, 490

[56] References Cited

U.S. PATENT DOCUMENTS

| | | | |
|---|---|---|---|
| 4,413,005 | 11/1983 | Goto et al. | 549/365 |
| 4,444,786 | 4/1984 | Goto et al. | 260/453.3 |

Primary Examiner—Henry R. Jiles
Assistant Examiner—Robert C. Whittenbaugh
Attorney, Agent, or Firm—Gerald L. Coon

[57] ABSTRACT

Pesticidal water-soluble aminoacid sulfenylated carbamates useful as broad spectrum insecticides and miticides, particularly useful as systemic insecticides.

20 Claims, No Drawings

PESTICIDAL WATER-SOLUBLE AMINOACID SULFENYLATED CARBAMATES

FIELD OF THE INVENTION

This invention relates to water-soluble aminoacid sulfenylated carbamates useful as broad spectrum insecticides and miticides.

DESCRIPTION OF THE INVENTION

This invention relates to compounds of the formula

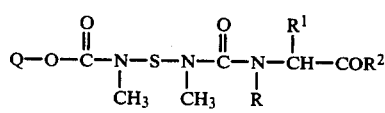

wherein

R is hydrogen or methyl; $R^1$ is hydrogen, alkyl, alkylthio, hydroxyalkyl, phenylalkyl, hydroxyphenylalkyl or indylalkyl containing from 1 to 6 aliphatic carbon atoms; or R and $R^1$ can be joined together to form an alkylene chain which may carry a hydroxy substituent and which completes a 4-6 membered heterocyclic ring;

$R^2$ is hydroxy, amino, or an alkali metal, alkaline earth metal, ammonium or alkyl-ammonium salt thereof; or alkoxy, alkylamino or dialkylamino wherein each alkyl moiety may contain from 1 to 6 carbon atoms; and Q is

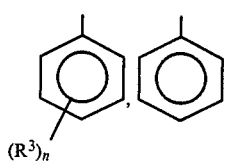 A or 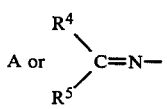

wherein n is 1, 2, 3 or 4;

each $R^3$ is independently halogen, alkyl, alkoxy, alkylthio, dialkylamino, alkoxyamido or 1,3-dioxalanyl wherein each $R^3$ independently contains no more than six aliphatic carbon atoms;

A is a saturated or unsaturated divalent chain composed of carbon atoms and not more than two oxygen atoms which completes a 5 or 6 membered heterocyclic or carbocyclic ring wherein the carbon atoms of the chain may be substituted with one or more $C_1$-$C_4$ alkyl substituents;

$R^4$ is aminocarbonyl, alkyl, alkylthioalkyl, alkoxyalkyl, cyanoalkyl, nitroalkyl, amidoalkyl, dialkylaminocarbonyl, aminocarbonylalkyl or dialkylaminocarbonylalkyl wherein each alkyl moiety can contain from one to six carbon atoms; and $R^5$ is hydrogen, alkylthio, cyanoalkylthio or amidoalkylthio wherein each alkyl moiety can contain from one to six carbon atoms.

The bicyclic radicals represented by Q include naphthyl, 5,6-dihydronaphthyl, 5,6,7,8-tetrahydronaphthyl, indenyl, indanyl, benzofuranyl, 2,3-dihydro-benzofuranyl, benzodioxanyl, benzothienyl, dihydrobenzothienyl and benzodioxolanyl, all of which may be optionally substituted with $C_{1-4}$ alkyl groups.

Preferred compounds of this invention include those in which $R^1$ is hydrogen, $C_1$-$C_4$ alkyl or $C_1$-$C_4$ hydroxyalkyl and $R_2$ is hydroxy, amino, alkoxy, alkylamino or dialkylamino wherein each alkyl moiety can contain from one to four carbon atoms.

Preferred bicyclic phenyl compounds are those in which Q is naphthyl, 2,3-dihydrobenzofuranyl or benzodioxanyl, optionally substituted with $C_1$-$C_4$ alkyl groups. Preferred monocyclic phenyl compounds are those in which the 2 or 4 phenyl positions are substituted with $C_1$-$C_4$ alkyl, alkoxy, alkylthio or dialkylamino and the 3 and 5 phenyl positions are unsubstituted or $C_1$-$C_4$ alkyl substituted. Preferred compounds of this invention when Q is

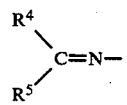

include those wherein $R^4$ is $C_1$-$C_4$ alkyl and $R^5$ is $C_1$-$C_4$ alkylthio.

Most preferred compounds of this invention include those wherein $R^1$ is hydrogen, $C_1$-$C_4$ alkyl or $C_1$-$C_4$ hydroxyalkyl; $R^2$ is hydroxyl or amino; and Q is 2,3-dihydro-2,2-dimethylbenzofuranyl or 1-methylthioacetimide.

The following table sets forth examples of compounds within the generic formula that will illustrate the compounds defined by this invention.

TABLE 1

$$Q-O-\overset{O}{\underset{}{C}}-\underset{CH_3}{\underset{|}{N}}-S-\underset{CH_3}{\underset{|}{N}}-\overset{O}{\underset{}{C}}-\underset{R}{\underset{|}{N}}-\overset{R^1}{\underset{|}{CH}}-COR^2$$

| Q | R | $R^1$ | $R^2$ |
|---|---|-----|-----|
| 2,2-dimethyl-2,3-dihydrobenzofuranyl | H | CH₃ | OH |
| 2,2-dimethyl-2,3-dihydrobenzofuranyl | H | H | OC₂H₅ |

TABLE 1-continued
$$Q-O-\overset{\overset{O}{\|}}{C}-\underset{\underset{CH_3}{|}}{N}-S-\underset{\underset{CH_3}{|}}{N}-\overset{\overset{O}{\|}}{C}-\underset{\underset{R}{|}}{N}-\overset{\overset{R^1}{|}}{C}H-COR^2$$
| Q | R | R¹ | R² |
|---|---|---|---|
| 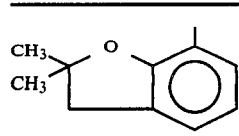 | H | CH(CH₃)₂ | OH |
| 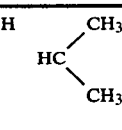 | H | CH₂OH | OH |
| 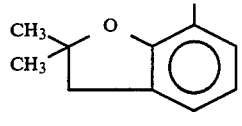 | H | H | OH |
| 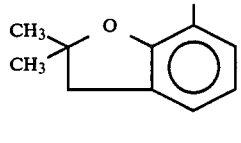 | H | H | NH₂ |
| 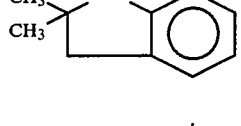 | H | H | 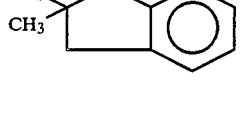 |
| 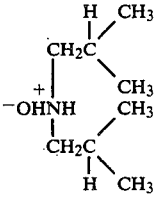 | H | CH₂CH₂SCH₃ | OH |
| 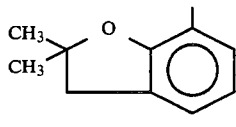 | H | CH₂C₆H₅ | OH |
| 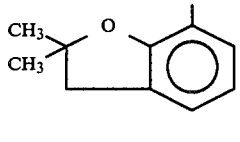 | H | 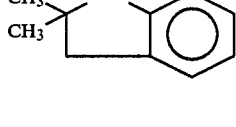 | OH |
| 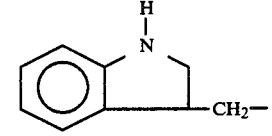 | H | CH₂COOH | OH |
| 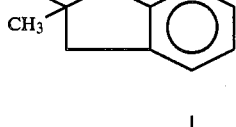 | | CH₂—CH₂—CH₂ | OH |

TABLE 1-continued $$Q-O-\underset{O}{\overset{O}{C}}-\underset{CH_3}{N}-S-\underset{CH_3}{N}-\underset{O}{\overset{O}{C}}-\underset{R}{N}-\underset{}{\overset{R^1}{C}H}-COR^2$$

| Q | R | R¹ | R² |
|---|---|---|---|
| (2,2-dimethyl-1,3-benzodioxol-4-yl, methyl-substituted) | H | H | OH |
| (2-(1-methylethoxy)methyl-phenyl, methyl-substituted) | H | CH₃ | OH |
| (4-methylnaphthalen-1-yl) | H | H | OC₂H₅ |
| (2-isopropyl-4-methyl-phenyl with NHCOOCH₃) | H | CH₂OH | OH |
| (2-isopropyl-phenyl, methyl-substituted) | | CH₂—CHOH—CH₂ | OH |
| (2-(1,3-dioxolan-2-yl)phenyl, methyl-substituted) | H | H | N(CH₃)₂ |
| (2,4,6-trimethyl-phenyl with N(CH₃)₂) | H | H | OH |
| (CH₃)(CH₃S)C=N— | H | H | OH |
| (CH₃)(CH₃S)C=N— | H | CH₃ | OH |
| (CH₃)(CH₃S)C=N— | H | CH₂OH | OH |

TABLE 1-continued

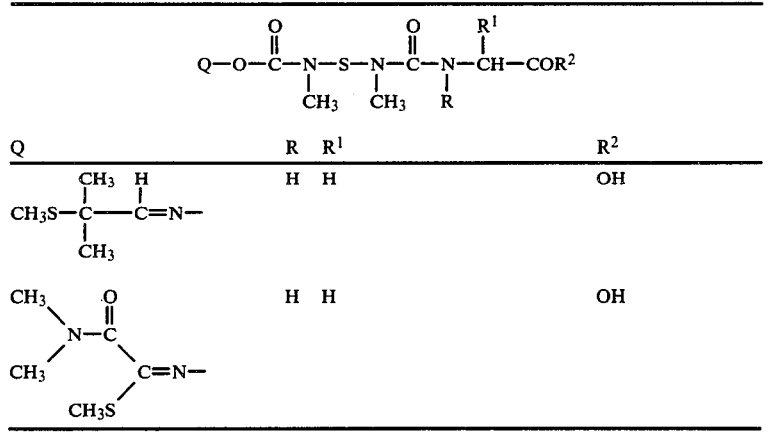

| Q | R | R¹ | R² |
|---|---|----|----|
| CH₃S—C(CH₃)(CH₃)—C(H)=N— | H | H | OH |
| (CH₃)₂N—C(=O)—C(CH₃)(SCH₃)=N— | H | H | OH |

The compounds of this invention exhibit broad spectrum insecticidal and miticidal activity. Since most the compounds of this invention are highly water soluble, they represent a distinct improvement over pesticidally active compounds with only a low level of water solubility. Working formulations of the water soluble compound can be easier and less expensive to prepare because there is no need for dispersing or emulsifying agents or organic diluents. Furthermore, the increased water solubility facilitates the application of the active compounds to the pest. For example, the compounds of this invention can be used for pest control by dissolving the compounds directly into water and then applying the aqueous solution to the pest by an appropriate method such as spraying. This avoids many of the problems associated with formulations such as crystallization, layer separation, aglomeration and the like. Additionally, non-water soluble pesticides are often not effective in situations where water solubility is necessary, e.g. for use in flooded rice fields.

The compounds of this invention can be prepared according to the following general reaction scheme:

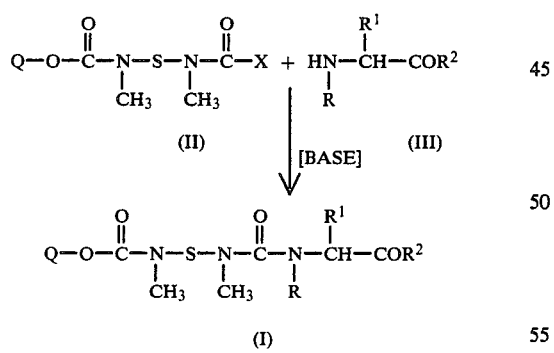

wherein X is halogen and Q,R,R¹ and R² are as defined above.

In this reaction an equivalent of the sulfenylated carbamate carbamoyl halide (II) is reacted with at least one equivalent of the aminoacid intermediate (III) in the presence of a base and a suitable solvent. A suitable solvent for the purposes of this invention is an inert organic solvent utilized alone or in an aqueous organic heterogeneous mixture. Suitable organic solvents include saturated or unsaturated aliphatic and aromatic hydrocarbons such as hexane, benzene or toluene; ethers such as diethyl ether or dioxane; and chlorinated aliphatic hydrocarbons such as dichloromethane. Other inert organic solvents, such as ketones and esters, may also be used.

When the reaction is conducted in a non-aqueous solvent system the base utilized is preferably an organic base such as triethylamine or pyridine. Inorganic bases, such as sodium bicarbonate, are preferably used when the reaction is conducted in a heterogeneous medium involving an aqueous phase.

In general, reaction pressures are not critical. The reaction can be conveniently conducted at subatmospheric, atmospheric or superatmospheric pressure.

The reaction can be conducted in the temperature range of from about $-20°$ C. to about $100°$ C. Preferably reaction temperatures are from about $-10°$ C. to about $30°$ C.

The sulfenylated carbamate cabamoyl halide (II) can be prepared according to known methods, as described, e.g., in U.S. Pat. No. 4,338,450.

The following specific examples are presented to more particularly illustrate the manner in which the compounds of this invention can be prepared.

EXAMPLE 1

The preparation of the compound of the formula:

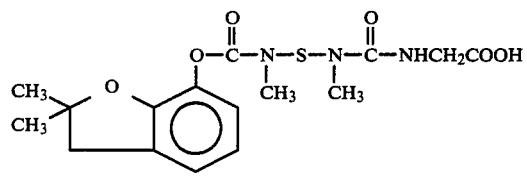

A solution of 6.56 g, 2,3-dihydro-2,2-dimethyl-7-benzofuranyl N-(N'-fluorocarbonyl-N'-methylaminosulfenyl)-N-methyl carbamate in 20 ml diethyl ether was added dropwise to a mixture of 1.5 g. glycine, 3.36 g sodium bicarbonate, 10 ml water and 10 ml diethyl ether stirred at about $-10°$ C. The mixture was then allowed to slowly attain room temperature and stirring continued for 16 hrs. The ether was stripped off under reduced pressure and the aqueous solution was filtered. The clear filtrate was acidified with 0.02 mole dilute hydrochloric acid, the precipitated solid product was separated by filtration, washed with a little cold water and then dried under vacuum to yield 3 g of the pure compound structurally depicted above, m.p. $55°-57°$ C. (CHCl₃). PMR (CDCl₃+TMS) $\delta=7.0-6.5$(3H), 3.9

(2H), 3.5(3H), 3.4(3H), 3.0(2H), 1.45(6H) and exchangeable signals at 7.7 (1H) and 7.3(1.5H, contains moisture).

EXAMPLE 2

The preparation of the compound of the formula:

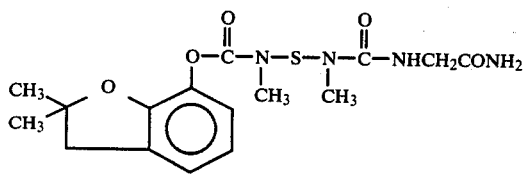

A mixture of 3 g. 2,3-dihydro-2,2-dimethyl-7-benzofuranyl N-(N'-fluorocarbonyl-N'-methylaminosulfenyl)-N-methylcarbamate, 0.8 g aminoacetamide and 0.9 g sodium bicarbonate in 30 ml dioxane was stirred at room temperature for about 16 hrs and then at 60° C. for 2 hrs. The solvent was stripped off under reduced pressure, the residue was treated with chloroform, washed with water, dried and then concentrated to yield 2.5 g of the crude compound structurally depicted above. The product was further purified by chromatography on silica gel eluting with 5% methanol in chloroform and was isolated as a white, hygroscopic solid, m.p. 58°-60° C.

PMR (CCl$_4$+CDCl$_3$+TMS) δ: 7.7(1H), 7.0–6.6(4H), 6.4(1H), 3.75(2H), 3.5(3H), 3.4(3H), 3.0(2H), 1.45(6H).

EXAMPLE 3

The preparation of the compound of the formula:

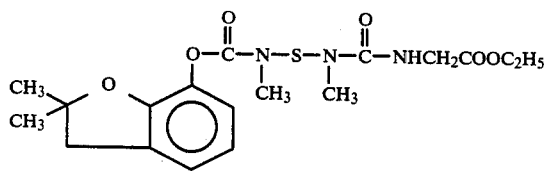

A mixture of 3.28 g, 2,3-dihydro-2,2-dimethyl-7-benzofuranyl N-(N'-flurocarbonyl-N'-methylaminosulfenyl)-N-methyl-carbamate and 1.4 g ethyl glycinate hydrochloride in 40 ml dichloromethane was stirred at 0° C. and 2.8 ml of triethylamine in 15 ml dichloromethane was added dropwise during 30 mts. at 0° C. The stirring continued at this temperature for 30 mts. more, the mixture was then allowed to slowly attain room temperature and stirring continued for about 16 hrs. The mixture was diluted with dichloromethane, washed with water, dried over anhydrous sodium sulfate and the solvent stripped off under reduced pressure to yield 4.5 g of the compound structurally depicted above in a sufficiently pure form. The compound was further purified by chromatography on silicagel eluting with 20% ethyl acetate in chloroform to yield a hygroscopic solid.

PMR (CCl$_4$+TMS) δ: 7.5(1H), 7.0–6.5(3H), 4.1(2H), 3.8(2H), 3.55(3H), 3.4(3H) 3.0(2H), 1.5(6H) and 1.25(3H).

EXAMPLE 4

The preparation of the compound of the formula:

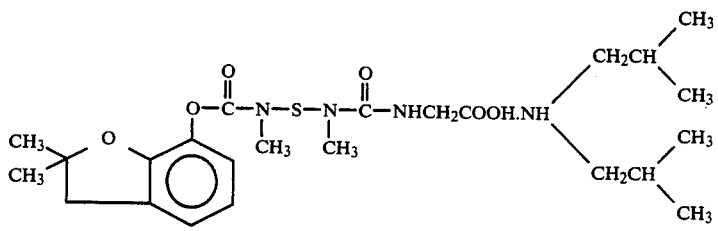

A solution of 0.88 ml diisobutylamine in 15 ml benzene was dropwise added to 1.92 g of the compound of Example 1 in 15 ml benzene stirred at room temperature. Stirring continued for 19 hrs. Benzene was stripped off under reduced pressure and residual crude product was recrystallized from dichloromethane/hexane mixture to yield 1.4 g pure compound of the above structure as a very hygroscopic solid.

PMR(CCl$_4$+CDCl$_3$+TMS) δ: 7.3(1H), 7.0–6.6(3H), 3.7(2H), 3.5(3H), 3.4(3H), 3.0(2H), 2.6(4H), 1.9(2H), 1.4(6H), 0.9(12H) and an exchangeable signal at 5.0 (>2H, contains moisture)).

EXAMPLES 5–12

In a manner similar to that employed in the preceding examples, and using the synthesis scheme previously disclosed, other compounds of this invention were prepared. The identity of the substituents on the generic formula and the analytical data are set forth in Table II below.

TABLE II

PHYSICAL AND SPECTRAL DATA OF REPRESENTATIVE COMPOUNDS

| Example | Formula | Physical and Spectral Data |
|---|---|---|
| | 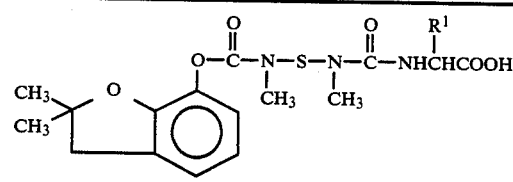 | |
| 5 | R$^1$<br>CH$_3$(DL) | M.P. 63.0–65.0° C.<br>PMR(CDCl$_3$ + CCl$_4$ + TMS) δ: 7.8–7.2 (2H exchangeable), 7.1–6.5(3H), |

TABLE II-continued
PHYSICAL AND SPECTRAL DATA OF REPRESENTATIVE COMPOUNDS

| Example | Formula | Physical and Spectral Data |
|---|---|---|
| | | 4.4–4.0(1H), 3.5(3H), 3.4(3H), 3.0(2H) and 1.5–1.3(9H). |
| 6 | $CH_3(L)$ | PMR($CDCl_3$ + $CCl_4$ + TMS) δ: 7.7(2H), 7.0–6.6(3H), 4.25(1H), 3.55(3H), 3.4(3H), 3.0(2H) and 1.4(9H). |
| 7 | $CHCH_3(DL)$<br>$CH_3$ | PMR($CDCl_3$ + $CCl_4$ + TMS) δ: 7.0–6.55(3H), 4.25(1H), 3.55(3H), 3.4(3h), 3.0(2H), 2.2(1H), 1.45(6H), 0.9(6H) and exchangeable signals at 7.5 (1H) and 6.5(2H, contains moisture). |
| 8 | $CH_2OH(DL)$ | M.P. 104.0–105.0° C.<br>PMR($CDCl_3$ + TMS) δ: 7.1–6.6 (3H), 4.4(1H), 3.85(2H), 3.55(3H), 3.4(3H), 3.0(2H), 1.45(6H) and exchangeable signals at 7.8(1H) and 4.8(>2H, contains moisture). |
| 9 | $CH_2OH(L)$ | M.P. 142.0–144.0° C.<br>PMR($CDCl_3$ + TMX) δ: 7.0–6.6 (3H), 4.4(1H), 3.8(2H), 3.5(3H), 3.4(3H), 3.0(2H), 1.5(6H) and exchangeable signals at 7.8 (1H) and 6.0(>2H, contains moisture). |

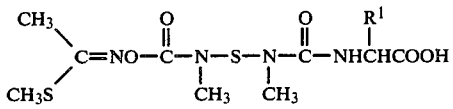

| Example | $R^1$ | |
|---|---|---|
| 10. | H | M.P. 67.0–68.0° C.'<br>PMR($D_2O$) δ (with reference to HOD set at 4.8): 3.9(2H), 3.5(3H), 3.45(3H), 2.5(3H) and 2.35(3H). |
| 11 | $CH_3(DL)$ | M.P. 55.0–66.0° C. hygroscopic solid<br>PMR($CDCl_3$ + $CCl_4$ + TMS) δ: 4.3(1H), 3.4(3H), 3.3(3H), 2.35(3H), 2.25(3H), 1.45(3H) and exchangeable signals at 9.7(1H) and 7.6(1H). |
| 12 | $CH_2OH(DL)$ | PMR($CDCl_3$ + DMSO—$D_6$ + TMS) δ: 4.4(1H), 3.9(2H), 3.45(3H), 3.35(3H), 2.4(3H), 2.3(3H) and exchangeable signals at 7.6(1H) and 3.9(>2H, containing moisture). |

Selected species of the compounds of this invention were evaluated to determine their pesticidal activity against mites and certain insects, including aphids, caterpillars, a beetle, a fly, a mosquito, a leafhopper, a planthopper, a stem borer and a gall midge.

Unless otherwise indicated, stock suspensions/solutions of test compounds were prepared by dissolving one gram of compound in 50 milliliters of acetone in which had been dissolved 0.1 gram (10 percent of the weight of the compound) of an alkylphenoxy polyethoxyethanol surfactant as an emulsifying or dispersing agent. The resulting solution was mixed into 150 milliliters of water to give roughly 200 milliliters of a suspension/solution containing the compound. The test concentrations in parts per million by weight employed in the tests described below were obtained by appropriate dilutions of the stock suspension in water.

BEAN APHID FOLIAGE SPRAY TEST

Adults and nymphal stages of the bean aphid (*Aphis fabae* Scope.) reared on potted dwarf nasturtium plants at 60°–70° F. and 50±5 percent relative humidity, constituted the test insects. For testing purposes, the number of aphids per pot was standardized to 100–150 by trimming plants containing excess aphids.

The test compounds were formulated by diluting the stock suspension with water to give a suspension containing 500 parts of test compound per million parts of final formulation.

The potted plants (one pot per compound tested) infested with 100–150 aphids, were placed on a revolving turntable and sprayed with 100–110 milliliters of test compound formulation by use of a spray gun set at 40 psi. air pressure. This application, which lasted 25 seconds, was sufficient to wet the plants to run-off. After spraying, the pots were placed on their sides on a sheet of white standard mimeograph paper which had been previously ruled to facilitate counting. Temperature and humidity in the test room during the 24 hour holding period were 68°–70° F. and 50±5% respectively. Aphids which fell onto the paper and were unable to remain standing after being uprighted were considered dead. Aphids remaining on the plants were observed closely for movement and those which were unable to move the length of the body upon stimulation by prodding were considered dead.

*Aphis craccivora* were also used as the test insects in some of the experiments under similar conditions.

SOUTHERN ARMYWORM LEAF SPRAY BAIT TEST

Larvae of the southern armyworm (*Spodoptera eridania* Cram.) reared on Tendergreen bean plants constituted the test insects. Tendergreen bean plants of standard height and age were placed on a revolving turntable and sprayed with 100-110 milliliters of test compound formulation containing 500 ppm of the test compound, by use of a spray gun set at 40 psi air pressure. This application, which lasted 25 seconds, was sufficient to wet the plants to run-off. When dry, the paired leaves were separated and each one was placed in a 9 centimeter petri dish lined with moistened filter paper. Five randomly selected larvae were introduced into each dish and the dishes were closed. The closed dishes were labeled and held at 80°-85° F. for five days. Untreated bean foliage was added for the larvae to feed after they had consumed treated leaf. Larvae which were unable to move the length of the body, even upon stimulation by prodding were considered dead.

TOBACCO CATERPILLAR

Late second instar tobacco caterpillar (*Spodoptera litura*) reared on castor leaves constituted the test insect. For testing purposes the number of insects per replicate was standardized to 5. Succulent castor leaves (approximately 25 sq. cm. area) were dipped in the formulated solution, containing 500 ppm of the test compound, for 10 seconds and then dried keeping ventral side up. After drying the leaves were transferred to clean petri plates keeping the dorsal side up and the larvae were released on the leaf and held for a period of 48 hrs at $27\pm$°C. and $70\pm10\%$ RH. After the exposure period all living larvae were transferred to fresh petri plates containing untreated castor leaves and fresh food was added at intervals of 24 hrs. Mortality count was made after a total of 5 days holding, i.e., 2 days exposure period and 3 days post-exposure period. Moribund insects were counted as dead and the mortality of treatments were corrected by using Abbott's formula.

MEXICAN BEAN BEETLE LEAF SPRAY TEST

Third instar larvae of the Mexican bean beetle (*Epilachna varivestis*, Muls.), reared on Tendergreen bean plants at a temperature of $80\pm5$° F. and $50\pm5$ percent relative humidity, were the test insects.

The test compounds were formulated by diluting the stock suspension with water to give a suspension containing 500 parts of test compound per million parts of final formulation. Tendergreen bean plants of standard height and age were placed on a revolving turntable and sprayed with 100-110 milliliters of test compound formulation by use of a spray gun set at 40 psi air pressure. This application, which lasted 25 seconds, was sufficient to wet the plants to run-off. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of $80\pm5$° F., for five days. Untreated bean leaf was provided after the larvae had consumed the treated leaf. Larvae which were unable to move the length of the body, even upon stimulation, were considered dead.

MITE FOLIAGE SPRAY AND SYSTEMATIC TEST

Adults and nymphal stages of two spotted mite (*Tetranychus urticae* Koch) reared on Tendergreen beans (under conditions $80\pm5$° F. and $50\pm5\%$ RH) constituted the test insects. Infested leaves from a stock culture were placed on the primary leaves of 2 bean plants 6-8 inches in height. A sufficient number of mites for testing (150-200) were transfered from the excised leaves to the fresh plants. Infested Tendergreen bean plants of standard height and age were placed on a revolving turntable and 100 ml of the formulated water mixture of the test compound (500 ppm) was applied to the plants by use of a spray gun with air pressure set at 40 psi during about 25 seconds. This volume of spray was sufficient to wet the plants to run-off. The potted plants were transferred to a 4-ounce paper container and 30 ml of the formulated compound (75 ppm) was poured into the pot.

The treated plants were held at $80\pm5$° F. and $50\pm5\%$ RH for a period of 7 days when mortality counts of motile forms were made. Microscopic examination of motile forms was made on one leaf from each of the two test plants. Any individual which was not capable of locomotion upon stimulation was considered dead.

FLY BAIT TEST

Four to six day old adult houseflies (*Musca domestica*, L.), reared according to the specifications of the Chemical Specialties Manufacturing Association (Blue Book, McNair-Dorland Co., N.Y. 1954, pages 243-244, 261) under controlled conditions of $80\pm5$° F. and $50\pm5$ percent relative humidity, were the test insects. The flies were immobilized by anesthetizing them with carbon dioxide. Twenty five immobilized individuals, males and females, were transferred to a cage consisting of a standard food strainer about five inches in diameter which was inverted over a wrapping paper covered surface. The test compounds were formulated by diluting the stock suspension with a 10 percent (by weight) sugar solution to give a suspension containing 500 parts of test compound per million parts of final formulation, by weight. Ten milliliters of the test formulation were added to a souffle cup containing a one-inch square of an adsorbent cotton pad. This bait cup was introduced and centered on the blotting paper under the food strainer prior to admitting the anesthetized flies. The caged flies were allowed to feed on the bait for twenty-four hours, at a temperature of $800\pm5$° F. and at a relative humidity of $50\pm5$ percent. Flies which showed no sign of movement on prodding were considered dead.

MOSQUITO LARVAE TOXICITY TEST

Fourth instar larvae of Culex Mosquito (*Culex quinquifasciatus*) constituted the test insect. A stock emulsion of 2500 ppm concentration of the test compound was made. In a 400 cc beaker, 1 ml of the stock solution was diluted with 224 ml of water. To this solution/suspension was added 25 ml of water containing 20 test insects, thus adjusting the final concentration of the test compound to 10 ppm. The beaker was kept at $27\pm1$° C. The mortality count was made after 20 hrs. of exposure period. All the moribund insects were counted as dead and the mortality percentages were corrected by using Abbott's formula.

GREEN LEAFHOPPER TOXICITY TEST

Freshly formed adults, both male and female of green leafhopper (*Nephotettix virescens* fam. cicadillidae) reared on potted paddy plants at 60 to 70% humidity and 27±3° C. temperature constituted the test insect. For testing purposes the number of GLH per replicate was standardized to 20.

Contact Toxicity Test

Test compounds were formulated by a standard procedure which involved dissolving the compounds (0.1 g) in acetone (100 ml) and then serial dilution with redistilled pure acetone and give the desired ppm concentration (500 ppm). One ml of the test dosages were applied on each filter paper circles placed on both cover and bottom of 9 cm petriplates. After 1 hr (drying period) insects were released and petriplates were kept in post treatment laboratory (temperature 27±1° C. and R.H. 70±5%) for 4 hrs and then mortality was counted. Moribund insects were counted as dead. In case of mortality in control, the mortality of treatments were corrected by using Abbott's formula.

Systemic Toxicity Test

Paddy plants were raised in 3" diameter plastic pots and after 7 DAT, formulated test compound dosages (500 ppm) in water and acetone emulsifier were applied at 10 ml per pot. After 48 hrs of treatment insects were released and encaged by ventilated glass tubes and kept in post treatment laboratory (temperature 27±1° C. and R.H. 70±5%). Mortality counts were made after 20 hrs of release.

BROWN PLANTHOPPER TOXICITY TEST

Newly formed mixed adults, both male and female of brown planthopper (*Nilaparvata lugens* Fam. Delphacidae) reared on potted paddy plants at 27±3° C. temperature and 60 to 70% relative humidity constituted the test insect. For testing purposes the number of insects per replicate was standardized to 20.

Contact Toxicity Test

Test method was the same as in the case of green leafhopper.

Systemic Toxicity Test

Test method was the same as in the case of green leafhopper.

STEM BORER TOXICITY TEST

Freshly hatched larvae of rice yellow stem borer (*Tryporyza, incertulas*) reared on potted paddy plants at 27±3° C. temperature and 70 to 80% relative humidity constituted the test insect. For testing purposes the number of insects per replicate was standardized to 20.

Contact Toxicity Test

Test compounds were formulated by a standard procedure which involved dissolving the compound (0.1 g) in acetone (100 ml) and then serial dilution with redistilled pure acetone to give the desired ppm concentration (5 ppm). Uniform dry films of test dosages were made in small vials by evaporation of 0.5 ml of insecticide solution. After 1 hr (drying period) insects were released in the vials and vials were kept in a dissicator having 27±1° C. and 100% R.H. After 30 mins. of exposure period the insects were transferred on to food (paddy cut stem) and again kept in a dessicator for 24 hrs (post treatment period). Mortality was counted by dissecting upon the paddy cut stem, treating moribund larvae as dead. In case of mortality in control, the mortality in treatments was corrected by using Abbott's formula.

Systemic Toxicity Test

Paddy plants were raised in 3" diameter plastic pots and after 7 DAT formulated test compound dosages (25 ppm) in water and acetone emulsifier were applied at 10 ml per pot. After 48 hrs of treatment freshly hatched larvae were released and pots were kept in post treatment laboratory (27±1° C. and 70±5% R.H.). Mortality counts were made after 20 hrs by dissecting open the seedlings.

GALL MIDGE TOXICITY TEST

Systemic Toxicity Test

Gall midge (*Orseolia oryzae* Fam. Cecidomyidae) were reared on potted paddy plants in the greenhouse at 27±3° C. temperature and 70 to 80% relative humidity. For testing purposes, 20 fertile gall midge eggs were placed on 12 day old paddy seedlings grown in 6" diameter plastic pots. The infested pots were then transferred to mist chamber for 72 hrs. After this hatching and maggot settling period the plants were treated with formulated test compound dosages (50 ppm) in water and acetone-emulsifier at 50 ml per pot. The treated pots were thereafter kept at 27±3° C. temperature and 70 to 80% R.H. Thirty days after release of the eggs, the gall (silver shoots) formed were counted and mortality of egg/maggots in relation to control were calculated for each treatment dosage.

Table III sets forth the results of the tests described above for selected compounds of this invention. The symbols used in Table III have the following meanings:

A=Excellent control (~80–100% mortality of target pest) at the screening dosage.

B=Moderate control (~40–79% mortality of target pest) at the screening dosage.

C=Poor or no control (<40% mortality of target pest) at the screening dosage. Compounds may be active at higher application rates since the screening dosage is an arbitrary limit.

—=Compound was not tested.

BA=Bean Aphid.
TC=Tobacco Caterpillar.
SAW=Southern Armyworm.
MBB=Mexican Bean Beetle.
M=Mite.
HF=Housefly.
CML=Culex Mosquito Larvae.
GLH=Green Leafhopper.
BPH=Brown Planthopper.
SB=Stem Borer.
GM=Gall midge.
(C)=Contact Activity.
(S)=Systemic Activity.

TABLE III

| Compound of Example # | BA | SAW | TC | MBB | BPH(C) | BPH(S) | GLH(C) | GLH(S) | SB(C) | SB(S) | GM(S) | HF | CML | M |
|---|---|---|---|---|---|---|---|---|---|---|---|---|---|---|
| 1. | A | A | A | A | A | A | A | A | C | A | A | A | A | A |
| 2. | A | — | A | — | B | A | B | A | A | A | — | — | A | — |
| 3. | A | A | A | A | A | A | B | A | A | A | — | A | A | — |
| 4. | A | — | A | — | C | A | A | A | C | A | — | — | A | C |
| 5. | A | — | A | — | A | A | A | A | A | A | — | — | A | — |
| 6. | A | — | B | — | B | A | B | A | B | A | — | — | A | — |
| 7. | A | — | A | — | C | A | C | A | A | A | — | — | A | — |
| 8. | A | — | A | — | B | A | B | A | B | A | — | — | A | — |
| 9. | A | — | A | — | B | A | B | A | B | A | — | — | A | — |
| 10. | A | A | A | A | A | A | A | B | A | B | — | A | B | A |
| 11. | A | A | A | A | C | B | A | C | A | B | — | A | C | A |
| 12. | A | A | — | A | — | — | — | — | — | — | — | A | — | C |

The data in Table III clearly illustrates the broad spectrum high level insecticidal and miticidal activity exhibited by the compounds of this invention, particularly with respect to their systemic insecticidal activity. It should be understood that the pests evaluated are representative of a wider variety of pests which can be controlled by the compounds of this invention.

The compounds contemplated in this invention may be applied according to methods known to those skilled in the art. Compositions containing the compounds as the active ingredient can comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a nonphytotoxic solvent such as acetone, xylene, or nitrobenzene and dispersing the toxicants in water with the aid of suitable surface active emulsifying and dispersing agent if desired.

The choice of dispersing and emulsifying agents and the amount employed is dictated by the nature of the composition and the ability of the agent to facilitate the dispersion of the compound. Generally, it is desirable to use as little of the agent as is possible. Nonionic, anionic, amphoteric or cationic dispersing and emulsifying agents may be employed; for example, the condensation products of alkylene oxides with phenol and organic acids, alkyl aryl sulfonates, complex ether alcohols, quaternary ammonium compounds, and the like.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

Because of the unique water solubility characteristics of most of the active compounds of this invention, either the technical materials or any appropriate formulation may be dissolved directly in water in sufficient amounts to attain the desired concentration levels. The water solution may then be applied to the pest by any conventional method known to those skilled in the art.

The required amount of the compound contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about ¼ to 15 pounds of active ingredients per acre.

It will be appreciated that mixtures of the active compounds of this invention may be employed as well as combinations of the active compounds of this invention with other biologically active compounds.

What is claimed is:

1. A compound of the formula:

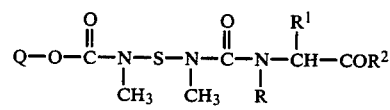

wherein

R is hydrogen or methyl; $R^1$ is hydrogen, alkyl, alkylthio, hydroxyalkyl, phenylalkyl, or hydroxyphenylalkyl containing from 1 to 6 aliphatic carbon atoms;

$R^2$ is hydroxy, amino, or an alkali metal, alkaline earth metal, ammonium or alkyl-ammonium salt thereof; or alkoxy, alkylamino or dialkylamino wherein each alkyl moiety may contain from 1 to 6 carbon atoms; and Q is

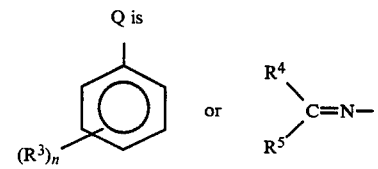

wherein n is 1, 2, 3 or 4;

each $R^3$ is independently halogen, alkyl, alkoxy, alkylthio, dialkylamino, or alkoxyamido wherein each $R^3$ independently contains no more than six aliphatic carbon atoms;

$R^4$ is aminocarbonyl, alkyl, alkylthioalkyl, alkoxyalkyl, cyanoalkyl, nitroalkyl, amidoalkyl, dialkylaminocarbonyl, aminocarbonylalkyl or dialkylaminocarbonylalkyl wherein each alkyl moiety can contain from one to six carbon atoms; and $R^5$ is hydrogen, alkylthio, cyanoalkylthio or amidoalkylthio wherein each alkyl moiety can contain from one to six carbon atoms.

2. A compound of the formula:

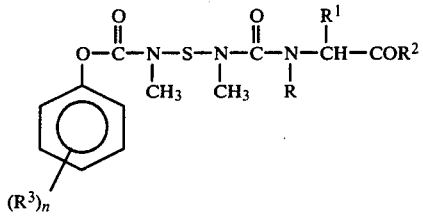

wherein

R is hydrogen or methyl; $R^1$ is hydrogen, alkyl, alkylthio, hydroxyalkyl, phenylalkyl, or hydroxyphenylalkyl containing from 1 to 6 aliphatic carbon atoms;

$R^2$ is hydroxy, amino, or an alkali metal, alkaline earth metal, ammonium or alkyl-ammonium salt thereof; or alkoxy, alkylamino or dialkylamino wherein each alkyl moiety may contain from 1 to 6 carbon atoms;

n is 1, 2, 3 or 4; and each $R^3$ is independently halogen, alkyl, alkoxy, alkylthio, dialkylamino, or alkoxyamido wherein each $R^3$ independently contains no more than six aliphatic carbon atoms.

3. A compound as recited in claim 2, wherein $R^1$ is hydrogen, $C_1$-$C_4$ alkyl or $C_1$-$C_4$ hydroxyalkyl.

4. A compound as recited in claim 2, wherein $R^2$ is hydroxy, amino, alkoxy, alkylamino or dialkylamino wherein each alkyl moiety can contain from one to four carbon atoms.

5. A compound of the formula:

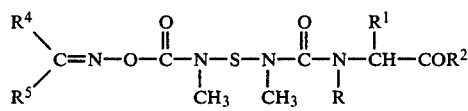

wherein

R is hydrogen or methyl; $R^1$ is hydrogen, alkyl, alkylthio, hydroxyalkyl, phenylalkyl, or hydroxyphenylalkyl containing from 1 to 6 aliphatic carbon atoms;

$R^2$ is hydroxy, amino, or an alkali metal, alkaline earth metal, ammonium or alkyl-ammonium salt thereof; or alkoxy, alkylamino or dialkylamino wherein each alkyl moiety can contain from 1 to 6 carbon atoms;

$R^4$ is aminocarbonyl, alkyl, alkylthioalkyl, alkoxyalkyl, cyanoalkyl, nitroalkyl, amidoalkyl, dialkylaminocarbonyl, aminocarbonylalkyl or dialkylaminocarbonylalkyl wherein each alkyl moiety can contain from one to six carbon atoms; and $R^5$ is hydrogen, alkylthio, cyanoalkylthio or amidoalkylthio wherein each alkyl moiety can contain from one to six carbon atoms.

6. A compound as recited in claim 5, wherein $R^1$ is hydrogen, $C_1$-$C_4$ alkyl or $C_1$-$C_4$ hydroxyalkyl.

7. A compound as recited in claim 5, wherein $R^2$ is hydroxy, amino, alkoxy, alkylamino or dialkylamino wherein each alkyl moiety can contain from one to four carbon atoms.

8. A compound as recited in claim 5, wherein $R^4$ is $C_1$-$C_4$ alkyl and $R^5$ is $C_1$-$C_4$ alkylthio.

9. A compound as recited in claim 1 having the formula

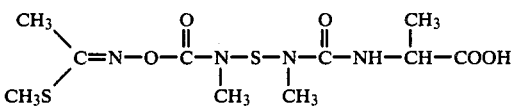

10. A compound as recited in claim 1 having the formula

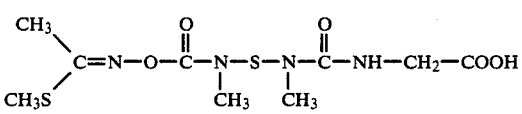

11. A composition comprising an acceptable carrier and an insecticidally or miticidally effective amount of a compound according to claim 1.

12. A composition comprising an acceptable carrier and an insecticidally or miticidally effective amount of a compound according to claim 2.

13. A composition comprising an acceptable carrier and an insecticidally or miticidally effective amount of a compound according to claim 5.

14. A composition comprising an acceptable carrier and an insecticidally or miticidally effective amount of a compound according to claim 9.

15. A composition comprising an acceptable carrier and an insecticidally or miticidally effective amount of a compound according to claim 10.

16. A method of controlling insects and mites which comprises subjecting them to an insecticidally or miticidally effective amount of a compound according to claim 1.

17. A method of controlling insects and mites which comprises subjecting them to an insecticidally or miticidally effective amount of a compound according to claim 2.

18. A method of controlling insects and mites which comprises subjecting them to an insecticidally or miticidally effective amount of a compound according to claim 5.

19. A method of controlling insects and mites which comprises subjecting them to an insecticidally or miticidally effective amount of a compound according to claim 9.

20. A method of controlling insects and mites which comprises subjecting them to an insecticidally or miticidally effective amount of a compound according to claim 10.

* * * * *